US012669486B2

(12) United States Patent　　　　　(10) Patent No.:　US 12,669,486 B2

Myron et al.　　　　　　　　　　　　(45) Date of Patent:　Jun. 30, 2026

---

(54) ETHANOL SENSORS FOR LOCATION-BASED USER DEVICE TRIGGERS

(71) Applicant: T-MOBILE INNOVATIONS LLC, Overland Park, KS (US)

(72) Inventors: Peter Philip Myron, New Braunfels, TX (US); Michael John Mitchell, North Bend, WA (US)

(73) Assignee: T-Mobile Innovations LLC, Overland Park, KS (US)

( * ) Notice: Subject to any disclaimer, the term of this patent is extended or adjusted under 35 U.S.C. 154(b) by 446 days.

(21) Appl. No.: 18/334,128

(22) Filed: Jun. 13, 2023

(65) Prior Publication Data

US 2024/0418692 A1　　Dec. 19, 2024

(51) Int. Cl.
　　*G01N 33/00*　　　　(2006.01)
　　*G06Q 50/40*　　　　(2024.01)

(52) U.S. Cl.
　　CPC ......... *G01N 33/0047* (2013.01); *G06Q 50/40* (2024.01)

(58) Field of Classification Search
　　CPC ........................... G06Q 50/40; G01N 33/0047
　　USPC ......................................................... 702/32
　　See application file for complete search history.

(56) References Cited

U.S. PATENT DOCUMENTS

| | | | |
|---|---|---|---|
| 8,455,262 B2 | 6/2013 | Sultan et al. | |
| 9,319,096 B1 | 4/2016 | Rifkin et al. | |
| 9,363,645 B2 | 6/2016 | Lavery | |
| 10,168,164 B2 | 1/2019 | Shelby et al. | |
| 2011/0188389 A1 | 8/2011 | Hedley et al. | |
| 2012/0142383 A1* | 6/2012 | Velusamy | H04H 60/52 455/507 |
| 2013/0210460 A1 | 8/2013 | Subramanian et al. | |
| 2016/0098650 A1 | 4/2016 | Ratti et al. | |

(Continued)

FOREIGN PATENT DOCUMENTS

| | | |
|---|---|---|
| CN | 112874299 A | 6/2021 |
| GB | 2610792 A | 3/2023 |
| WO | 2021064743 A1 | 4/2021 |

OTHER PUBLICATIONS

Non-Final Office Action received for U.S. Appl. No. 18/334,908, mailed on Sep. 24, 2025, 20 pages.

*Primary Examiner* — John H Le

(74) *Attorney, Agent, or Firm* — Shook Hardy & Bacon L.L.P.

(57)　　　　　　　　ABSTRACT

The technologies discussed herein relate to methods, systems, media, etc., for automatically triggering a user device action based on utilizing one or more ethanol sensor devices. In embodiments, an ethanol sensor device can detect ethanol vapor concentrations and determine whether the concentration is above a threshold. In embodiments, the ethanol sensor device can transmit the detected concentrations to one or more servers, which can cause the user device to initiate an action based on a concentration level that is above the threshold. For example, the server can provide one or more ride hailing services, such that the server initiates the user device action that includes providing, for display on a user interface of the user device, one or more selectable ride hailing transportation options from a location corresponding to the user device. In some embodiments, the server provides services corresponding to physical or mental health.

20 Claims, 6 Drawing Sheets

(56)             References Cited

U.S. PATENT DOCUMENTS

| | | |
|---|---|---|
| 2016/0204879 A1 | 7/2016 | Niewczas et al. |
| 2017/0184537 A1* | 6/2017 | Umasankar ........ G01N 27/4065 |
| 2017/0213459 A1 | 7/2017 | Ogaz |
| 2017/0223170 A1 | 8/2017 | Winebrand et al. |
| 2017/0356749 A1 | 12/2017 | Shelby et al. |
| 2018/0235581 A1 | 8/2018 | Vianello |
| 2019/0135177 A1* | 5/2019 | Farrell ..................... B60Q 9/00 |
| 2019/0159109 A1 | 5/2019 | Bloechl et al. |
| 2019/0173590 A1 | 6/2019 | Mufti |
| 2019/0178976 A1 | 6/2019 | Xiong et al. |
| 2019/0204110 A1 | 7/2019 | Dubielzyk et al. |
| 2019/0317068 A1* | 10/2019 | Beck ................. G01N 33/0063 |
| 2019/0383627 A1 | 12/2019 | Nangeroni et al. |
| 2020/0036451 A1 | 1/2020 | Gilson |
| 2021/0274333 A1 | 9/2021 | Petersen |
| 2021/0410066 A1 | 12/2021 | Shi et al. |
| 2022/0163336 A1 | 5/2022 | Rahematpura et al. |
| 2022/0255636 A1 | 8/2022 | Shi et al. |
| 2023/0245558 A1 | 8/2023 | Monegan |

* cited by examiner

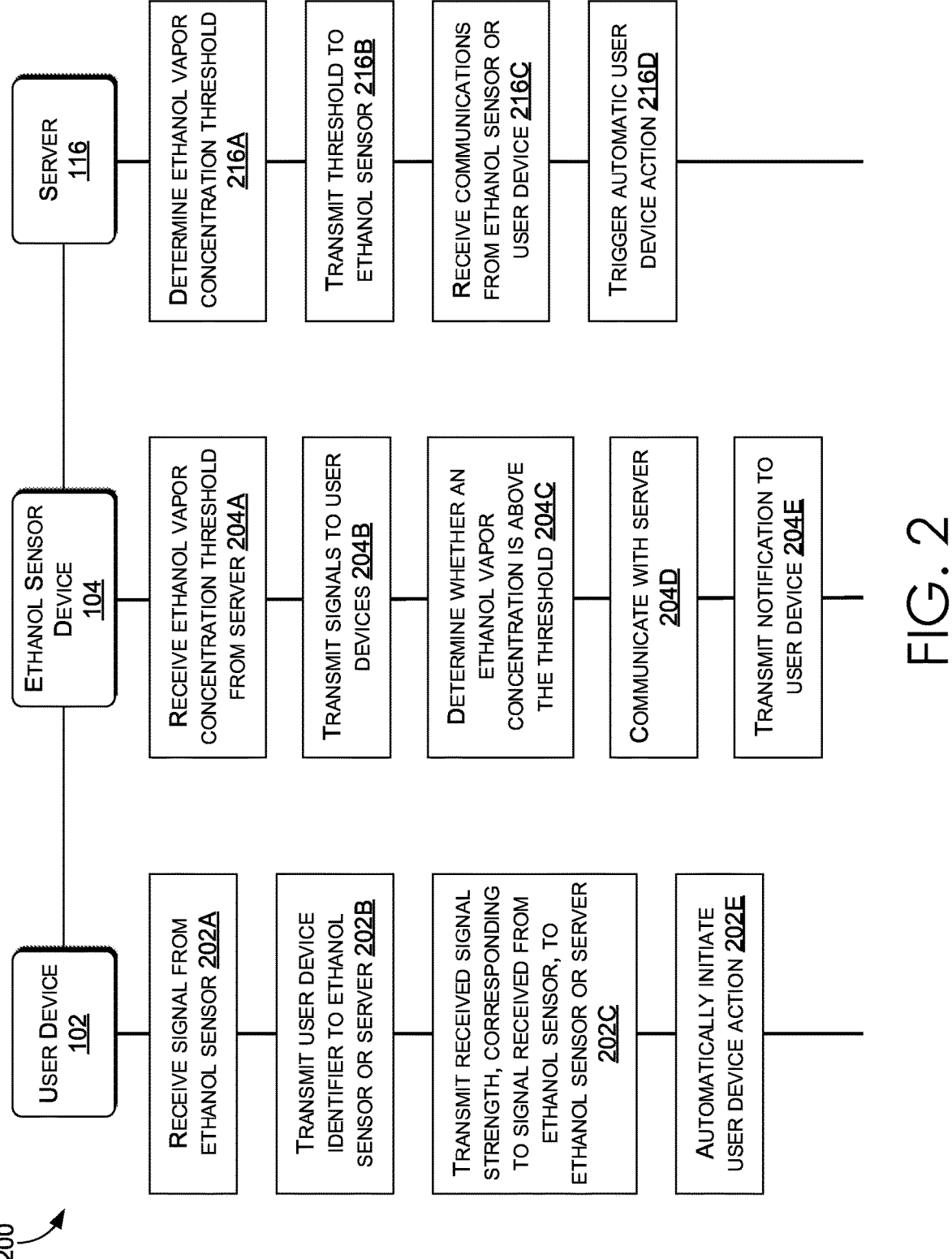

SERVER 116

DETERMINE ETHANOL VAPOR CONCENTRATION THRESHOLD 216A

TRANSMIT THRESHOLD TO ETHANOL SENSOR 216B

RECEIVE COMMUNICATIONS FROM ETHANOL SENSOR OR USER DEVICE 216C

TRIGGER AUTOMATIC USER DEVICE ACTION 216D

ETHANOL SENSOR DEVICE 104

RECEIVE ETHANOL VAPOR CONCENTRATION THRESHOLD FROM SERVER 204A

TRANSMIT SIGNALS TO USER DEVICES 204B

DETERMINE WHETHER AN ETHANOL VAPOR CONCENTRATION IS ABOVE THE THRESHOLD 204C

COMMUNICATE WITH SERVER 204D

TRANSMIT NOTIFICATION TO USER DEVICE 204E

USER DEVICE 102

RECEIVE SIGNAL FROM ETHANOL SENSOR 202A

TRANSMIT USER DEVICE IDENTIFIER TO ETHANOL SENSOR OR SERVER 202B

TRANSMIT RECEIVED SIGNAL STRENGTH, CORRESPONDING TO SIGNAL RECEIVED FROM ETHANOL SENSOR, TO ETHANOL SENSOR OR SERVER 202C

AUTOMATICALLY INITIATE USER DEVICE ACTION 202E

DETECT THAT ETHANOL VAPOR CONCENTRATION IS ABOVE A THRESHOLD ~302

DETECT THAT A USER DEVICE IS WITHIN A THRESHOLD DISTANCE ~304

TRANSMIT A NOTIFICATION TO THE USER DEVICE ~306

TRANSMIT INFORMATION TO SERVER ~308

400

RECEIVE SIGNAL FROM ETHANOL SENSOR DEVICE —402

TRANSMIT USER DEVICE IDENTIFIER OR RECEIVED SIGNAL STRENGTH —404

RECEIVE NOTIFICATION FROM ETHANOL SENSOR DEVICE —406

AUTOMATICALLY INITIATE USER DEVICE ACTION —408

500
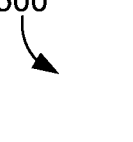
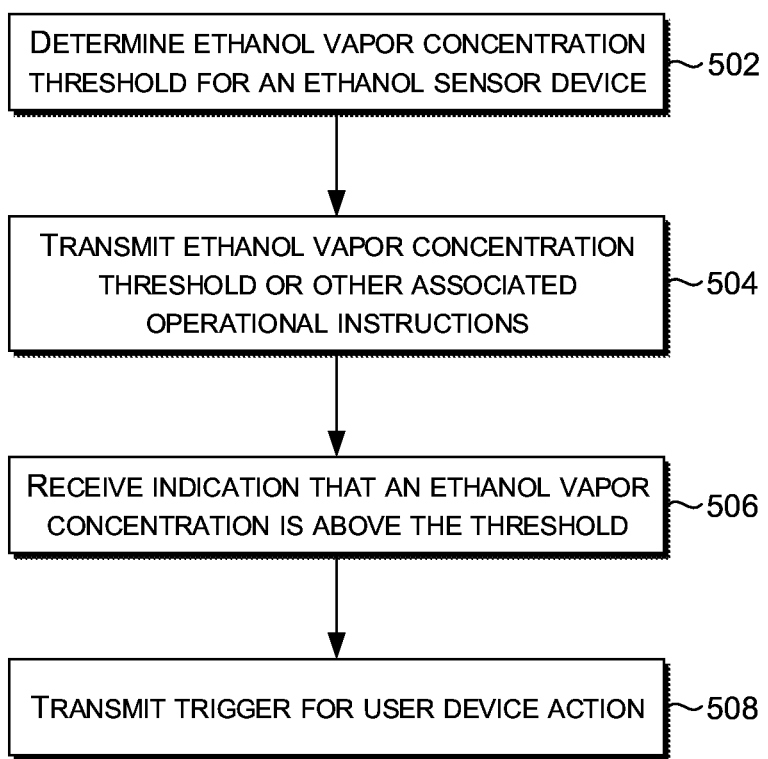
DETERMINE ETHANOL VAPOR CONCENTRATION THRESHOLD FOR AN ETHANOL SENSOR DEVICE —502
TRANSMIT ETHANOL VAPOR CONCENTRATION THRESHOLD OR OTHER ASSOCIATED OPERATIONAL INSTRUCTIONS —504
RECEIVE INDICATION THAT AN ETHANOL VAPOR CONCENTRATION IS ABOVE THE THRESHOLD —506
TRANSMIT TRIGGER FOR USER DEVICE ACTION —508
FIG. 5

ETHANOL SENSORS FOR LOCATION-BASED USER DEVICE TRIGGERS

SUMMARY

A high-level overview of various aspects of the technology disclosed herein is provided here for that reason, to provide an overview of the disclosure and to introduce a selection of concepts that are further described in the Detailed Description section below. This Summary is not intended to identify key features or essential features of the claimed subject matter, nor is it intended to be used as an aid in isolation to determine the scope of the claimed subject matter. The present disclosure is directed, in part, to systems and methods corresponding to ethanol sensors for location-based user device triggers, substantially as shown in and/or described in connection with at least one of the figures, and as set forth more completely in the claims.

In aspects set forth herein, and at a high level, the systems, methods, and media disclosed herein correspond to initiating user device actions based on utilizing one or more ethanol sensor devices. For example, an ethanol sensor device can include a semi-conductor-based sensor, an electrochemical sensor, an infrared sensor, another type of ethanol vapor sensor, or one or more combinations thereof. In some embodiments, the ethanol sensor device is coupled to an object (e.g., a wall, a door, a ceiling, a support structure). In some embodiments, the ethanol sensor device is located within an indoor environment and is within a threshold distance with one or more other ethanol sensor devices. The ethanol sensor can communicate with user devices and servers (e.g., a server providing ride hailing services) based on the ethanol vapor concentration detections. For example, based on the server detecting that the ethanol vapor concentration is above a threshold, the ethanol sensor device can transmit associated information to a server, such that the server can trigger a user device action (e.g., via an application that is downloaded onto the user device) based on the detected ethanol vapor concentrations.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

Aspects of the present disclosure are described in detail herein with reference to the attached figures, which are intended to be exemplary and non-limiting, wherein:

FIG. 2 illustrates an example operational environment for the user device, ethanol sensor, and corresponding server, in accordance with embodiments herein;

FIG. 5 depicts another flow diagram of an example server method for the location-based user device triggers, in accordance with aspects herein.

DETAILED DESCRIPTION

Figure 1:
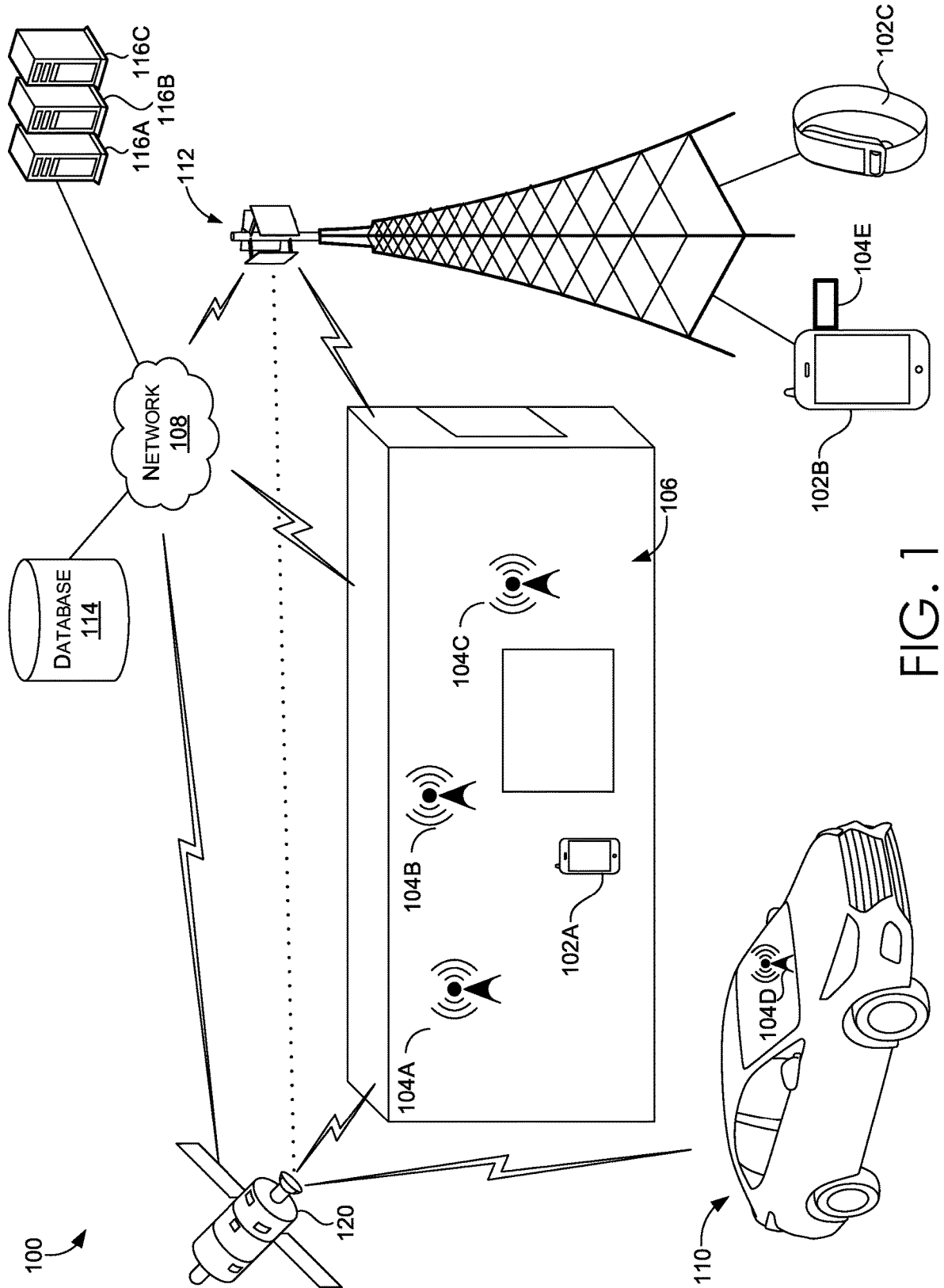
FIG. 1 depicts an example environment corresponding to the ethanol sensors for location-based user device triggers, in accordance with embodiments herein.

The subject matter of embodiments of the invention is described with specificity herein to meet statutory requirements. However, the description itself is not intended to limit the scope of this patent. Rather, the inventors have contemplated that the claimed subject matter might be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Throughout this disclosure, several acronyms and shorthand notations are employed to aid the understanding of certain concepts pertaining to the associated system and services. These acronyms and shorthand notations are intended to help provide an easy methodology of communicating the ideas expressed herein and are not meant to limit the scope of embodiments described in the present disclosure. The following is a list of these acronyms:

3G Third-Generation Cellular Communication System
4G Fourth-Generation Cellular Communication System
5G Fifth-Generation Cellular Communication System
6G Sixth-Generation Cellular Communication System
AOA Angle of Arrival
API Application Programming Interface
CA Carrier Aggregation
CD-ROM Compact Disk Read Only Memory
CDMA Code Division Multiple Access
DVD Digital Versatile Discs
EEPROM Electrically Erasable Programmable Read Only Memory
EMF Electromagnetic Field
EMS Enhanced Messaging Service
eNB Evolved Node B
Ev-DO Evolution-Data Optimized
FD-MIMO Full-Dimension Multiple-Input Multiple-Output
gNB Next Generation Node B
GPRS General Packet Radio Service
GSM Global System for Mobile communications
HSS Home Subscriber System
IEEE Institute of Electrical and Electronics Engineers
IP Internet Protocol
LTE Long Term Evolution
MAC Media Access Control
MIMO Multiple-Input Multiple-Output
MME Mobility Management Entity
MMS Multimedia Messaging Service
MU-MIMO Multi-User Multiple-Input Multiple-Output
NR New Radio
OTDOA Observed Time Difference of Arrival
PC Personal Computer
PDA Personal Digital Assistant
RAM Random Access Memory
RAN Radio Access Node RF Radio-Frequency
ROM Read Only Memory
RRC Radio Resource Control
RRU Remote Radio Unit
RSRP Reference Signal Received Power
RSRQ Reference Signal Received Quality
RSSI Received Signal Strength Indicator
RTT Round-Trip Time
SMS Short Message Service
TCP Transmission Control Protocol
TDMA Time Division Multiple Access
TOA Time of Arrival
UDP User Datagram Protocol
UE User Equipment
VONR Voice over NR
VOLTE Voice over LTE
WiMAX Worldwide Interoperability for Microwave Access In addition, words such as "a" and "an," unless otherwise indicated to the contrary, may also include the plural as well as the singular. Thus, for example, the constraint of "a feature" is satisfied where one or more features are present. As such, an element in the singular may refer to "one or more."

Further, the term "or" includes the conjunctive, the disjunctive, and both (a or b thus includes either a or b, as well as a and b).

In addition, the term "some" may refer to "one or more."

The term "combination" (e.g., one or more combinations thereof) may refer to, for example, "at least one of A, B, and C"; "at least two of A, B, or C" (e.g., AA, AB, AC, BB, BA, BC, CC, CA, CB); "each of A, B, and C"; and may include multiples of A, multiples of B, or multiples of C (e.g., CCABB, ACBB, ABB, etc.). Other combinations may include more or less than three options associated with the A, B, and C examples.

The term "communicating" (e.g., the user device communicating, a server communicating) may refer to, for example, receiving or transmitting a signal, data, a message, another type of communication, or one or more combinations thereof.

Unless specifically stated otherwise, descriptors such as "first," "second," and "third," for example, are used herein without imputing or otherwise indicating any meaning of priority, physical order, arrangement in a list, or ordering in any way, but are merely used as labels to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name.

Additionally, "user device," as used herein, is a device that has the capability of using a wireless telecommunications network, and may also be referred to as a "computing device," "mobile device," "user equipment" (UE), or "wireless communication device." A user device, in some aspects, may take on a variety of forms, such as a PC, a laptop computer, a tablet, a mobile phone, a PDA, a server, an Internet of Things device, any other device capable of communicating with other devices (e.g., by transmitting or receiving a signal) using a wireless communication, or one or more combinations thereof. A user device may be, in an embodiment, similar to user devices 102A-102C described herein with respect to FIG. 1. A user device may also be, in another embodiment, similar to user device 600, described herein with respect to FIG. 6.

As noted above, the user device may include Internet of Things devices, such as one or more of the following: a sensor (e.g., a temperature sensor), controller (e.g., a lighting controller, a thermostat), an appliance (e.g., a smart refrigerator, a smart air conditioner, a smart alarm system), other Internet of Things devices, or one or more combinations thereof. Internet of Things devices may be stationary, mobile, or both. In some aspects, the user device is associated with a vehicle (e.g., a video system in a car capable of receiving media content stored by a media device in a house when coupled to the media device via a local area network). In some aspects, the user device comprises a medical device, a location monitor, a clock, a drone, a remote weather station, another wireless communication device, or one or more combinations thereof.

In embodiments, a user device discussed herein may be configured to communicate using one or more of 4G (e.g., LTE), 5G, 6G, another generation communication system, or a combination thereof. In some aspects, the UE has a radio that connects with a 4G cell site but is not capable of connecting with a higher generation communication system. In some aspects, the UE has components to establish a 5G connection with a 5G gNB, and to be served according to 5G over that connection. In some aspects, the user device may be an E-UTRAN New Radio-Dual Connectivity (ENDC) device. ENDC allows a user device to connect to an LTE eNB that acts as a master node and a 5G gNB that acts as a secondary node. As such, in these embodiments, the ENDC device may access both LTE and 5G simultaneously, and in some cases, on the same spectrum band.

The term "ethanol sensor device" may refer to, for example, a device capable of detecting ethanol concentrations in air, such as few parts per million (ppm) up to several hundred ppm, a few hundred ppm up to several thousand ppm, tens of ppm to several thousand ppm, a few hundred to high percentages, another concentration range, or one or more combinations thereof. In some embodiments, an ethanol sensor device may include a semi-conductor-based sensor, a catalytic sensor, an electrochemical sensor, an infrared sensor, another type of ethanol vapor sensor, or one or more combinations thereof. In some embodiments, the ethanol sensor device can communication over a network (e.g., via a cell site or satellite). In some embodiments, ethanol sensor devices can communicate among each other (e.g., via a short-range wireless technology standard, via a millimeter wave technology standard). In some embodiments, the ethanol sensor device is a standalone device or a device capable of connecting to a user device via an input port of the user device. In some embodiments, the ethanol sensor device is integrated into a wearable user device.

As used herein, the term "cell site" generally refers to one or more cellular base stations, nodes, RRUs control components, other components configured to provide a wireless interface between a wired network and a wirelessly connected user device, or a combination thereof. A cell site may comprise one or more nodes (e.g., eNB, gNB, other nodes, or one or more combinations thereof) that are configured to communicate with user devices. In some aspects, the cell site may include one or more band pass filters, radios, antenna arrays, power amplifiers, transmitters/receivers, digital signal processors, control electronics, GPS equipment, other equipment, or a combination thereof. A cell site or a node (e.g., eNB or gNB) corresponding to the cell site may comprise one or more of a macro base station, a small cell or femtocell base station, a relay base station, another type of base station, or one or more combinations thereof. In aspects, the cell site may be configured as FD-MIMO, massive MIMO, MU-MIMO, cooperative MIMO, 3G, 4G, 5G, 6G, another generation communication system, or one or more combinations thereof. In addition, the cell site may operate in an extremely high frequency region of the spectrum (e.g., from 30 GHz to 300 GHz), also known as the millimeter band.

A "telecommunication service" may refer to a satellite communication service, a microwave communication service, a millimeter wave communication service, a voice service (e.g., VoIP, an audio conferencing service), a messaging service (e.g., SMS messages, MMS messages, instant messaging messages, an EMS service messages), a data service (e.g., an internet service, an emailing service, a file transferring service), a wireless service through a wireless network, a cloud-based service, a managed service operated by a particular provider (e.g., a managed network service, a managed security service, a managed hosting service), other types of telecommunication services, or one or more combinations thereof.

A "vehicle" may refer to a vehicle having a motor or a vehicle that does not have a motor. For example, a "vehicle" may include a car (e.g., a sedan, a truck, another type of car, a gas-powered vehicle, an electric-powered vehicle, a diesel-powered vehicle, vehicle powered by another source of energy, etc.), a motorcycle, a bicycle, a scooter, or other types of vehicles.

Embodiments of the technology described herein may be embodied as, among other things, a method, system, or computer-program product. Accordingly, the embodiments may take the form of a hardware embodiment, or an embodiment combining software and hardware. An embodiment that takes the form of a computer-program product can include computer-useable instructions embodied on one or more computer-readable media.

Computer-readable media include both volatile and nonvolatile media, removable and nonremovable media, and contemplate media readable by a database, a switch, and various other network devices. Network switches, routers, and related components are conventional in nature, as are means of communicating with the same. By way of example, and not limitation, computer-readable media comprise computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, DVD, holographic media or other optical disc storage, magnetic cassettes, magnetic tape, magnetic disk storage, and other magnetic storage devices. These memory components can store data momentarily, temporarily, or permanently.

Communications media typically store computer-useable instructions—including data structures and program modules—in a modulated data signal (e.g., a modulated data signal referring to a propagated signal that has one or more of its characteristics set or changed to encode information in the signal). Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

By way of background, prior relevant technologies have not identified user devices within a predetermined area having a concentration of ethanol vapors exceeding a threshold. In addition, prior relevant technologies have not initiated automatic user device actions based on determining the ethanol concentration within the predetermined area and based on identifying user devices. In this way, the prior relevant technologies have had challenges that involve decreases in quality of service and user device experiences. According to the United States Department of Transportation, each day, about 37 people in the United States die in drunk-driving crashes—i.e., one person every 39 minutes. In 2021, 13,384 people died in alcohol-impaired driving traffic deaths—a 14% increase from 2020. These deaths were all preventable. The technology discussed herein can alleviate these problems and shortcomings by increasing the quality of service and user device experience.

In one embodiment, a system for utilizing ethanol sensor devices to initiate a user device trigger is provided. For example, the system may comprise a plurality of ethanol sensor devices each coupled to an object and each configured to wirelessly detect ethanol vapors, wherein each of the plurality of ethanol sensor devices are positioned within a threshold distance from at least another one of the plurality of ethanol sensor devices. The system also comprises one or more processors corresponding to each of the plurality of ethanol sensor devices, the one or more processors configured to perform operations. The operations comprise detecting, by a first ethanol sensor device of the plurality of ethanol sensor devices, an ethanol vapor concentration that is above a threshold. The operations also comprise detecting, by the first ethanol sensor device, a user device that is within a threshold distance from the first ethanol sensor device. Based on detecting that the ethanol vapor concentration is above the threshold and detecting that the user device is within the threshold distance, transmitting, by the first ethanol sensor device, a notification to the user device. Based on detecting that the ethanol vapor concentration is above the threshold and detecting that the user device is within the threshold distance, transmitting, by the first ethanol sensor device, information to a server, such that the server can initiate an action via an application that is downloaded onto the user device.

In another embodiment, a method is provided for triggering an action by a user device based on communications with an ethanol sensor device. For example, the method may comprise receiving, by the user device, a signal from the ethanol sensor device. The method may also comprise transmitting, by the user device, a user device identifier and a received signal strength to the ethanol sensor device or a server associated with the ethanol sensor device. The method may also comprise receiving, by the user device, a notification from the ethanol sensor device, the notification received based on the ethanol sensor device detecting that an ethanol vapor concentration is above a threshold and based on the ethanol sensor device detecting that the user device is within a threshold distance from the ethanol sensor device. Based on transmitting the user device identifier and the received signal strength, automatically initiating, by the user device, an action via an application that is downloaded onto the user device.

Another embodiment may comprise one or more non-transitory computer storage media having computer-executable instructions embodied thereon, that when executed by at least one processor, cause the at least one processor to perform a method for initiating a user device trigger based on communications with an ethanol sensor device. For example, the method may comprise determining, by one or more servers in communication with one or more ethanol sensor devices, an ethanol vapor concentration threshold for the one or more ethanol sensor devices based on a location of each of the one or more ethanol sensor devices and historical user device traffic corresponding to the location of each of the one or more ethanol sensor devices. The method may also comprise transmitting, by the one or more servers, a first ethanol vapor concentration threshold determined for a first ethanol sensor device of the one or more ethanol sensor devices to the first ethanol sensor device. The method may also comprise receiving, by the one or more servers, an indication from the first ethanol sensor device that a first ethanol vapor concentration is above the first ethanol vapor concentration threshold. The method may also comprise receiving, by the one or more servers, a user device identifier for a user device. Based receiving the user device identifier and the indication that the first ethanol vapor concentration is above the first ethanol vapor concentration threshold, transmitting, by the one or more servers, a trigger for an application that is downloaded onto the user device and that initiates an action by the application.

Turning now to FIG. 1, example environment 100 comprises user devices 102A-102C, ethanol sensor devices 104A-104E, building 106, network 108, vehicle 110, cell site 112, database 114, servers 116A-116C, and satellite 120. Example environment 100 is but one example of a suitable environment for the technology described herein, and is not intended to suggest any limitation as to the scope of use or functionality of the invention. Neither should the environment 100 be interpreted as having any dependency or requirement relating to any one or combination of components illustrated. As an example, another embodiment of example environment 100 may include more or less user devices, ethanol sensor devices, networks, cell sites, databases, servers, or satellites. In yet another example, although building 106 is illustrated as an indoor environment, in other implementations, the ethanol sensor devices 104A-104E may be positioned throughout an outdoor environment.

In embodiments, one or more of the user devices 102A-102C may include one or more of a unit, a station, a terminal, a client, etc., or one or more combinations thereof. One or more of the user devices 102A-102C may, in some embodiments, include a wireless local loop station, an IoT device, an Internet of Everything device, a machine type communication device, an evolved or enhanced machine type communication device, another type of user device, or one or more combinations thereof. The user devices 102A-102C (e.g., the machine type communication device or the evolved or enhanced machine type communication device) may include, for example, one or more robots, drones, remote devices, sensors (e.g., one or more ethanol sensors), meters, monitors, location tags, etc., that may communicate with cell site 112, another device (e.g., the ethanol sensor devices 104A-104E), or some other entity (e.g., the servers 116A-116C). In some embodiments, one or more of the user devices 102A-102C may be implemented in various objects such as appliances, vehicles, meters, or other objects. In some embodiments, one or more of the user devices 102A-102C may, at one time or another, act as a relay, base station, (e.g., an unmanned aerial vehicle acting as an aerial base station), or other network components (e.g., macro eNBs or gNBs, small cell eNBs or gNBs, or relay base stations). As such, in some embodiments, one or more signals transmitted from the unit, station, terminal, client, wireless local loop station, IoT device, Internet of Everything device, machine type communication device, evolved or enhanced machine type communication device, user device implemented in an object, another type of user device, or one or more combinations thereof, can be received by one or more of the cell site 112, the satellite 120, the servers 116A-116C, the ethanol sensor devices 104A-104E, the database 114, another network component, or one or more combinations thereof.

In embodiments, user devices 102A-102C or ethanol sensor devices 104A-104E may wirelessly communicate via network 108. For example, user devices 102A-102C or ethanol sensor devices 104A-104E can communicate using one or more wireless communication standards. For example, the user devices 102A-102C or ethanol sensor devices 104A-104E may be configured to communicate using a wireless networking (e.g., Wi-Fi), one or more peer-to-peer wireless communication protocols (e.g., Bluetooth, Wi-Fi peer-to-peer, other peer-to-peer protocols, or one or more combinations thereof), a cellular communication protocol (e.g., GSM, UMTS (associated with WCDMA or TD-SCDMA air interfaces, for example), LTE, LTE-A, 5G NR, HSPA, 3GPP2 CDMA2000 (e.g., 1×RTT, 1×EV-DO, HRPD, eHRPD)), other communication protocols, or one or more combinations thereof. In some embodiments, the user devices 102A-102C or ethanol sensor devices 104A-104E may additionally or alternatively communicate using one or more global navigational satellite systems (GNSS, such as GPS or GLONASS for example), one or more mobile television broadcasting standards (e.g., ATSC-M/H or DVB-H), another wireless communication protocol, or one or more combinations thereof. In some embodiments, the user devices 102A-102C or ethanol sensor devices 104A-104E may include separate transmit or receive chains (e.g., including separate antennas and other radio components) for each wireless communication protocol with which it is configured to communicate.

In embodiments, one or more of the ethanol sensor devices 104A-104E may include a metal oxide semiconductor sensor (e.g., tin dioxide, tungsten oxide), a field-effect transistor sensor, a chemiresistor, a conducting polymer sensor, another type of semiconductor-based sensor, or one or more combinations thereof. In some embodiments, one or more of the ethanol sensor devices 104A-104E may include an amperometric sensor, a potentiometric sensor, a conductometric sensor, an ion-selective field-effect transistor, another type of electrochemical sensor, or one or more combinations thereof. In some embodiments, one or more of the ethanol sensor devices 104A-104E may include a non-dispersive infrared sensor, a tunable diode laser absorption spectroscopy sensor, another type of infrared ethanol vapor sensor, or one or more combinations thereof.

Figure 6:
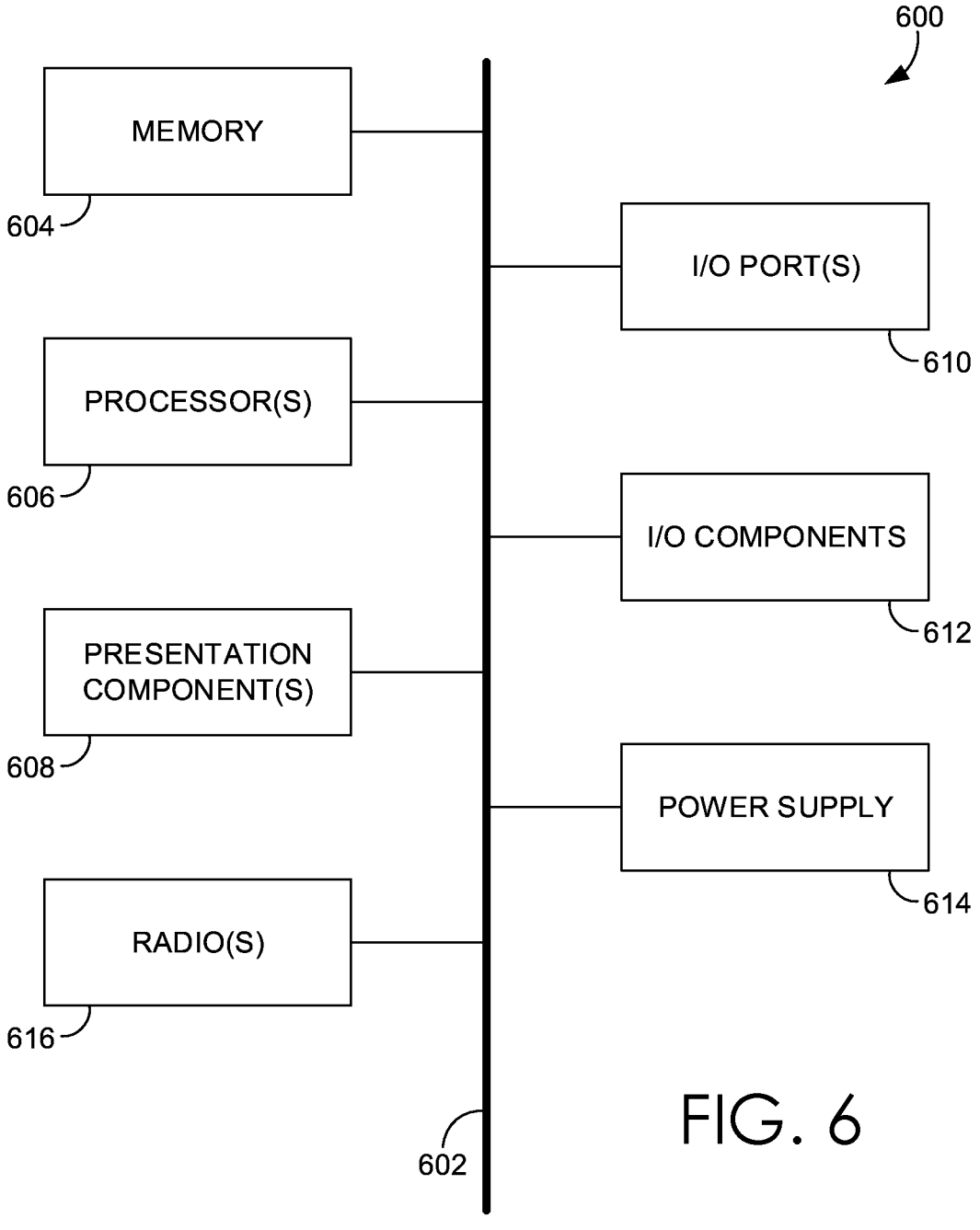
FIG. 6 depicts an example user device suitable for use in implementations of the present disclosure, in accordance with aspects herein.

In example environment 100, ethanol sensor devices 104A-104C are positioned within the building 106, ethanol sensor device 104D is positioned within vehicle 110, and ethanol sensor device 104E is a removable device that is coupled to the user device 102B via an input port (e.g., I/O ports 610 of FIG. 6). In some embodiments, the ethanol sensor devices 104A-104C are coupled (e.g., coupled together in a way in which the coupled pair work in conjunction or interact with each other) or affixed (e.g., attached, sticking, fastened) to an object within the building 106. For example, one of the ethanol sensor devices 104A-104C may be affixed to a wall, a door, an exit, a ceiling, the floor, another object, or one or more combinations thereof. As another example, one of the ethanol sensor devices

104A-104C may be coupled to a smart door or a smart appliance. In embodiments, each of the ethanol sensor devices 104A-104C may be within a threshold distance from each other, or within a threshold distance from one of the other ethanol sensor devices 104A-104C. In embodiments, a set of ethanol sensor devices may be located within a threshold distance from each other and positioned adjacent to an exit or an alcohol serving area, wherein each of the set of ethanol sensor devices communicate with each other to determine an ethanol vapor concentration for a particular area within the building 106. In some embodiments, an ethanol sensor device may be a wearable user device (e.g., such as user device 102C).

In some embodiments, ethanol sensor device 104D may be coupled to vehicle 110 (e.g., coupled via an input port of the vehicle). In some embodiments, ethanol sensor device 104D may be affixed to vehicle 110 (e.g., affixed to the driver's wheel, a dashboard, or another location inside the vehicle 110). In some embodiments, ethanol sensor device 104D may be integrated into the vehicle 110 (e.g., a smart vehicle, an electric vehicle) and located adjacent to the driver's seat. In other embodiments, the vehicle 110 may be a motorcycle, an airplane, another aerial or terrestrial vehicle, a bicycle, a scooter, another type of vehicle, or one or more combinations thereof. In some embodiments, the vehicle 110 includes a plurality of ethanol sensor devices that are each in communication with each other, and wherein each of the plurality of ethanol sensor devices in the vehicle 110 communicate to determine an ethanol vapor concentration for a particular area within the vehicle 110 that is adjacent to the driver's seat. For example, each of those ethanol sensor devices may be within a particular threshold from each other.

The network 108 may provide one or more telecommunication services via the cell site 112, the satellite 120, another network component, or one or more combinations thereof. In some embodiments, network 108 may provide one or more telecommunication services via the ethanol sensor devices 104A-104C. The one or more telecommunication services may include, for example, the transfer of information without the use of an electrical conductor as the transferring medium. A wireless telecommunication service may correspond to the transfer of information via radio waves (e.g., Bluetooth®), satellite communication, infrared communication, microwave communication, Wi-Fi, millimeter wave communication, mobile communication, another type of communication, or a combination thereof. In embodiments, the telecommunication service may include one or more of a voice service, a message service (e.g., SMS messages, MMS messages, instant messaging messages, an EMS service messages), a data service, other types of wireless telecommunication services, or a combination thereof. In embodiments, the one or more telecommunication services may be provided by one or more communication providers. For example, user device 102A may correspond to a user who is registered or subscribed to a first telecommunication service provider to utilize one or more telecommunication services, and the user device 102B may correspond to a user registered or subscribed to a second telecommunication service provider that is different from the first telecommunication service provider. In some embodiments, ethanol vapor concentration thresholds, user device action triggers, other information, or one or more combinations thereof, are transmitted by one or more of the servers 116A-116C over the network 108 via a telecommunication service.

In some embodiments, the example operating environment 100 may support enhanced broadband communications, ultra-reliable (e.g., mission critical) communications, low latency communications, communications with low-cost and low-complexity devices, another type of communication, or one or more combinations thereof. In some embodiments, one or more communications between one or more devices in example operating environment 100 (e.g., communications between one or more of the user devices 102A-102C and one or more servers 116A-116C, communications between one or more servers 116A-116C and one or more ethanol sensor devices 104A-104E, communications among the ethanol sensor devices 104A-104E, communications among the servers 116A-116C) may correspond to the enhanced broadband communication, ultra-reliable communication, low latency communication, another type of communication, or one or more combinations thereof.

As one example, one or more of the ethanol vapor concentration thresholds may be transmitted by one or more of the servers 116A-116C over the network 108 via the enhanced broadband communication, ultra-reliable communication, low latency communication, another type of communication, or one or more combinations thereof. As another example, one or more of the servers 116A-116C may receive, over the network 108 (e.g., via the enhanced broadband communication, ultra-reliable communication, low latency communication, another type of communication, or one or more combinations thereof) a user device identifier corresponding to one or more of the user devices 102A-102C (e.g., a server may receive the user device identifier from an ethanol sensor device or the user device). In embodiments, a user device identifier may include a user device identifier corresponding to an application downloaded onto that user device, one or more portions of a telephone number (e.g., an area code, a country code, a line number), a user device model identifier, a user device version identifier, a serial number, an international mobile equipment identity, another type of user device identifier, or one or more combinations thereof.

In embodiments, example environment 100 can utilize both licensed and unlicensed radio frequency bands. For example, the example environment 100 may employ License Assisted Access, LTE-Unlicensed radio access technology, or NR technology in an unlicensed band (e.g., 5 GHz industrial, scientific, and medical band). When operating in unlicensed radio frequency bands, cell site 112, one or more of servers 116A-116C, satellite 120, one or more of user devices 102A-102C, one or more of ethanol sensor devices 104A-104E, another network component, or one or more combinations thereof, may employ carrier sensing for collision avoidance and detection. In some examples, operations in unlicensed bands may be based on a carrier aggregation configuration and component carriers operating in a licensed band. Operations in unlicensed spectrum may include downlink transmissions, uplink transmissions, P2P transmissions, D2D transmissions, another type of unlicensed spectrum operation, or one or more combinations thereof. As such, one or more communications-between or among two or more of cell site 112, one or more of servers 116A-116C, satellite 120, one or more of user devices 102A-102C, one or more of ethanol sensor devices 104A-104E, another network component, or one or more combinations thereof—may correspond to a licensed or unlicensed radio frequency band, a 5 GHz industrial band, a 5 GHz scientific band, a 5 GHz medical band, a particular carrier aggregation configuration of a licensed band, a P2P transmission, a D2D transmission, another type of spectrum operation, or one or more combinations thereof.

As one example, one or more of the servers 116A-116C may transmit the one or more of the ethanol vapor concentration thresholds over the network 108 via the licensed or unlicensed radio frequency band, the 5 GHz industrial band, the 5 GHz scientific band, the 5 GHz medical band, the particular carrier aggregation configuration of a licensed band, the P2P transmission, the D2D transmission, another type of spectrum operation, or one or more combinations thereof. In yet another example, the one or more of the servers 116A-116C may transmit user device action triggers (e.g., via the licensed or unlicensed radio frequency band, the 5 GHz industrial band, the 5 GHz scientific band, the 5 GHz medical band, the particular carrier aggregation configuration of a licensed band, the P2P transmission, the D2D transmission, another type of spectrum operation, or one or more combinations thereof) to a user device based on receiving a communication from an ethanol sensor device or the user device.

In embodiments, the network 108 may correspond to one or more of 3G, 4G, 5G, 6G, another generation communication system, 802.11, millimeter waves, FD-MIMO, massive MIMO, MU-MIMO, cooperative MIMO, another type of communication system, or one or more combinations thereof. Additionally, other wireless communication protocols may be utilized in conjunction with aspects described herein. For example, embodiments of the present technology may be used with one or more wireless communication protocols or standards, including, but not limited to, CDMA 1×Advanced, GPRS, Ev-DO, TDMA, GSM, WiMAX technology, LTE, LTE Advanced, other technologies and standards, or one or more combinations thereof. As such, one or more communications—between or among two or more of cell site 112, one or more of servers 116A-116C, satellite 120, one or more of user devices 102A-102C, one or more of ethanol sensor devices 104A-104E, another network component, or one or more combinations thereof—may correspond to one or more of 3G, 4G, 5G, 6G, another generation communication system, 802.11, millimeter wave communication, FD-MIMO, massive MIMO, MU-MIMO, cooperative MIMO, another type of communication protocol, one or more wireless communication protocols or standards (e.g., CDMA 1×Advanced, GPRS, Ev-DO, TDMA, GSM, WiMAX technology, LTE, LTE Advanced, other technologies and standards), or one or more combinations thereof. As one example, the one or more of the servers 116A-116C may transmit the determined ethanol vapor threshold or the user device action trigger via one or more of 3G, 4G, 5G, 6G, another generation communication system, 802.11, millimeter wave communication, FD-MIMO, massive MIMO, MU-MIMO, cooperative MIMO, another type of communication protocol, one or more wireless communication protocols or standards (e.g., CDMA 1×Advanced, GPRS, Ev-DO, TDMA, GSM, WiMAX technology, LTE, LTE Advanced, other technologies and standards), or one or more combinations thereof.

In embodiments, one or more cell sites 112 can provide the one or more wireless communication services via network 108, the network 108 comprising one or more telecommunication networks, or a portion thereof. A telecommunication network might include an array of devices or components (e.g., one or more cell sites 112). The network 108 can include multiple networks, and the network can be a network of networks. In embodiments, the network 108 is a core network, such as an evolved packet core, which may include at least one MME, at least one serving gateway, and include at least one Packet Data Network gateway. The MME may manage non-access stratum (e.g., control plane) functions such as mobility, authentication, and bearer management for other devices associated with the evolved packet core. In an embodiment, the network 108 comprises at least two core networks associated with a legacy LTE network and a 5G network. The at least two core networks may each operate one or more public land mobile networks, which may operate in each of the at least two core networks (e.g., one public land mobile network operates in each of an evolved packet core and a 5G core network). In embodiments, different core networks may be provided for different types of services, for different types of customers, for different types of traffic, to provide different levels of Quality of Service, or one or more combinations thereof. The network 108 can comprise any communication network providing voice, message, or data service(s), such as, for example, a 1× circuit voice, a 3G network (e.g., CDMA, CDMA2000, WCDMA, GSM, UMTS), a 4G network (WiMAX, LTE, HSDPA), a 5G network, a 6G network, another generation network, or one or more combinations thereof.

Components of the network 108, such as terminals, links, and nodes (as well as other components), can provide connectivity in various implementations. For example, components of the network 108 may include core network nodes, relay devices, integrated access and backhaul nodes, macro eNBs, small cell eNBs, gNBs, relay cell sites, satellites, other network components, or a combination thereof. The network 108 may interface with one or more cell sites through one or more wired or wireless backhauls. Furthermore, user devices can utilize the network 108 to communicate with other devices (e.g., a user device(s), a server(s), ethanol sensor device(s), etc.) through the one or more cell sites 112.

The one or more cell sites 112 may include one or more cells, band pass filters, radios, antennas, antenna arrays, power amplifiers, transmitters/receivers, digital signal processors, control electronics, GPS equipment, and the like. In some aspects, the cell site 112 may comprise one or more macro cells (providing wireless coverage for users within a large geographic area). For example, macro cells may correspond to a coverage area having a radius of approximately 1-15 miles or more, the radius measured at ground level and extending outward from an antenna at the cell site. In some aspects, cell site 112 may comprise, or be in communication with, one or more small cells (providing wireless coverage for users within a small geographic area). For example, a small cell may correspond to a coverage area having a radius of approximately less than three miles, the radius measured at ground level and extending outward from an antenna at the cell site. In embodiments, cell site 112 is in communication with a plurality of in-door small cells. In some embodiments, one or more of the ethanol sensor devices 104A-104E are in-door small cells located within building 106.

Database 114 may include stored data received from one or more of user devices 102A-102C, ethanol sensor devices 104A-104E (e.g., historical oxygen concentrations detected by the ethanol sensor devices 104A-104E, historical nitrogen concentrations detected by ethanol sensor devices 104A-104E, historical carbon dioxide concentrations detected by ethanol sensor devices 104A-104E), cell site 112, servers 116A-116C, satellite 120, another network component, or one or more combinations thereof. In some embodiments, database 114 is a centralized database including a single server. In some embodiments, database 114 is a distributed database having multiple locations that are in communication via the network 108. In some embodiments, the database 114 includes a hierarchical database (e.g., organized in a tree-like structure having parent-child relationships between data elements). For example, user device actions or user device action triggers other information, or one or more combinations thereof, may be stored in the hierarchical database 114 as having a child relationship to data elements corresponding to the ethanol vapor concentrations, ethanol vapor concentration thresholds, user device identifiers, other information, or one or more combinations thereof, stored within database 114. As another example, one or more of user devices 102A-102C may transmit a user device identifier corresponding to the respective user device over the network 108 based on one or more communications with one or more of the ethanol sensor devices 104A-104E, wherein the user device identifier is stored in the hierarchical database 114 as having a child relationship to an identifier of an ethanol sensor device.

In some embodiments, the database 114 is a network database (e.g., using a network model to represent the stored data), an object-oriented database (e.g., which defines objects by class and allowing object retrieval based on attributes and relationships), an in-memory database, a spatial database, a blockchain database, a relational database (e.g., Google Cloud SQL), non-relational databases having a flexible schema design with horizontal scalability for large volumes of unstructured or semi-structured data (e.g., MongoDB), a key-value store (e.g., Redis), a document database (e.g., CouchDB), a columnar database (e.g., Apache Cassandra, Google BigQuery), a graph database (e.g., Neo4j), a time-series database (e.g., InfluxDB), another type of database, or one or more combinations thereof. In embodiments, one or more of user devices 102A-102C, ethanol sensor devices 104A-104E, cell site 112, servers 116A-116C, satellite 120, another network component, or one or more combinations thereof, may access, organize, or query the database 114.

In embodiments, one or more of the servers 116A-116C may be a web server (e.g., having one or more server nodes for balancing load and redundancy), such that the user device action triggers a user device to automatically launch a webpage hosted by the web server, wherein the webpage provides services or coupons to services corresponding to physical or mental health (e.g., ways to improve physical or mental health for alcoholics), wherein the trigger initiates the user device action of providing, for display on a user interface of the user device, one or more selectable physical or mental health services or coupons to those services. In other embodiments, the web server (e.g., one or more of servers 116A-116C) provides a webpage offering fast food to purchase or another type of good or service. In embodiments, one or more of the servers 116A-116C may be an application server (e.g., providing database connectivity, transactional management services, messaging services, other communication services), such that the user device action trigger causes an application downloaded onto the user device to open and provide offers for services corresponding to physical or mental health. In other embodiments, the application server (e.g., one or more of servers 116A-116C) provides offers, discounts, or services related to food (e.g., fast food for delivery), video games, designer products, or other types of goods or services. In embodiments, one or more of the servers 116A-116C may be a database server (e.g., providing access to database 114, permitting data transmission to or retrieval from database 114), such that the user device action trigger causes the user device to automatically initiate communication with the database server (e.g., an SQL server, MySQL). For example, the user device can provide the database server with user device identifiers, data within a calendar of the user device related to alcohol classes or meetings, email data related to alcohol services, other alcohol related data, or one or more combinations thereof.

In embodiments, one or more of the servers 116A-116C may be a mail server (e.g., having one or more transfer agents, having one or more mail delivery or retrieval agents), such that the user device action trigger causes the user device to automatically transmit or receive a message (e.g., an email) from (or to) the mail server). In some embodiments, one or more of the servers 116A-116C may be a proxy server (e.g., providing load balancing, access control, filtering, etc., between or among servers 116A-116C), such that the proxy server can manage user device and ethanol sensor device communications with another server. For example, the proxy server may determine user device or ethanol sensor device priorities (e.g., based on timing of a communication, based on a user device identifier or ethanol sensor identifier) for access to the other server.

In embodiments, servers 116A-116C may include one or more processors, memory, a data store (e.g., a hardware drive, a solid-state drive), a network interface for transmitting or receiving communications over network 108, another server component, or one or more combinations thereof. In embodiments, one or more of the servers 116A-116C may include a network switch, a router, a load balancer, a firewall, another type of network equipment, or one or more combinations thereof. In embodiments, one or more of the servers 116A-116C may include a runtime environment (e.g., for execution of an application in which one of the user devices 102A-102C may automatically launch upon receiving the user device action trigger), a middleware component (e.g., to facilitate a messaging service via the application automatically launched by the user device), a web-based interface, a command-line tool, another software component, or one or more combinations thereof.

In some embodiments, servers 116A-116C may have a central architecture (e.g., each server located within a threshold distance of the other servers or each located within a particular area) or a distributed architecture (e.g., each server being in a different location and connected via network 108 or a portion thereof). In some embodiments, servers 116A-116C may have a client-server architecture, wherein at least one of the servers responds to requests from another server, a peer-to-peer architecture wherein a node of each of the servers 116A-116C share resources or services, a three-tier architecture including a presentation layer, application layer, and data layer, a microservices architecture, a clustered architecture, a grid architecture, another type of architecture, or one or more combinations thereof. For example, in some embodiments, upon one or more of the user devices 102A-102C receiving the user device trigger, that respective user device can launch an application (e.g., a ride hailing application, an alcohol support application) provided by application layer 116A and presentation layer 116B. In response to the respective user device launching the application, that user device may transmit information over the network 108 (e.g., payment information), and data layer 116C may facilitate an associated service (e.g., a reservation of the ride hailing service, the purchase of a physical or mental health service related to alcohol).

In embodiments, satellite 120 may communicate with the cell site 112, user devices 102A-102C, ethanol sensor devices 104A-104E, database 114, servers 116A-116C, another network component, or one or more combinations thereof. In some embodiments, satellite 120 may include a space vehicle or communication satellite. Satellite 120 may be any suitable type of communication satellite configured to relay communications between different devices within environment 100. Satellite 120 may be or include a space satellite, a balloon, a dirigible, an airplane, a drone, an unmanned aerial vehicle, another type of satellite, or one or more combinations thereof. In some examples, the satellite 120 may be in a geosynchronous or geostationary earth orbit, a low earth orbit, a medium earth orbit, another type of orbit, or one or more combinations thereof. In some embodiments, satellite 120 may be a multi-beam satellite configured to provide service for multiple service beam coverage areas in a predefined geographical service area. The satellite 120 may be any distance away from the surface of the earth. In one non-limiting example, satellite 120 may correspond to a geosynchronous earth orbiting satellite or may have a satellite operating configuration corresponding to multiple service beam coverage areas in a predefined geographical service area.

In some embodiments, the one or more servers 116A-116C can receive information from or transmit information (e.g., ethanol vapor concentration thresholds, ride hailing service reservation information, other types of service reservation information related to alcohol consumption) to one or more of the user devices 102A-102C or one or more of the ethanol sensor devices 104A-104E via satellite 120 (e.g., the space satellite, balloon, dirigible, airplane, drone, unmanned aerial vehicle, multi-beam satellite, another type of satellite, or one or more combinations thereof). For example, this information transmitted or received via the satellite 120 may correspond to a free space optical link, a microwave link, electromagnetic wave signals via millimeter wave signals, optical signals via a laser, another type of communication link, a wireless common public radio interface protocol, a dedicated wireless front haul protocol developed for high-altitude-to-high-altitude, another protocol, or one or more combinations thereof. In some embodiments, the satellite 120 can demodulate received information and transmit that demodulated information, encode or decode data received from the user devices 102A-102C (or the ethanol sensor devices 104A-104E) or encode or decode data transmitted to the user devices 102A-102C (or the ethanol sensor devices 104A-104E), modulate the data once transmitted, perform another type of satellite or regenerative transponder function on data, or one or more combinations thereof.

FIG. 2 illustrates example operational environment 200 comprising user device 102, ethanol sensor device 104, and server 116. In embodiments, at 202A, the user device 102 can receive a signal from the ethanol sensor device 104 (e.g., based on a location of the user device 102 relative to the ethanol sensor device 104, based on the user device 102 being within a threshold distance from the ethanol sensor device 104, based on the ethanol sensor device determining an ethanol vapor concentration). In some embodiments, the signal is a near field signal, a Bluetooth signal, a millimeter wave signal, a Wi-Fi signal, a Wi-Fi peer-to-peer signal, a cellular communication protocol signal, another type of signal, or one or more combinations thereof. In some embodiments, the signal includes a request for a user device identifier, a request for a received signal strength corresponding to the signal, another type of request, or one or more combinations thereof.

At 202B, the user device 102 transmits a user device identifier to the server 116 or the ethanol sensor device 104. In embodiments, a user device identifier may correspond to an application downloaded onto the user device 102, one or more portions of a telephone number (e.g., an area code, a country code, a line number) of the user device 102, a user device model identifier, a user device version identifier, a serial number, an international mobile equipment identity, another type of user device identifier, or one or more combinations thereof. In some embodiments, the user device identifier is transmitted to the server 116 based on receiving a server identifier or instructions via the signal received from the ethanol sensor device 104.

At 202C, the user device 102 transmits a received signal strength to the server 116 or the ethanol sensor device 104. In some embodiments, the user device 102 can also transmit additional signal determinations, such as a quality of the signal received, for example. In some embodiments, user device 102 transmits the information corresponding to the signal received from the ethanol sensor device 104 to the ethanol sensor device 104 or the server 116 via mmWaves, FD-MIMO, massive MIMO, 3G, 4G, 5G, 6G, another type of Generation, 802.11 protocols and techniques, another type of wireless communication, or one or more combinations thereof. In some embodiments, user device 102 transmits the information corresponding to the signal received from the ethanol sensor device 104 to the ethanol sensor device 104 or the server 116 via enhanced broadband communications, ultra-reliable (e.g., mission critical) communications, low latency communications, communications with low-cost and low-complexity devices, another type of communication, or one or more combinations thereof.

At 202D, the user device 102 can automatically initiate a user device action based on instructions received from the server 116 and based on the ethanol sensor device 104 detecting the ethanol vapor concentration that is above the threshold. In some embodiments, the user device action is initiated via an application that is downloaded onto the user device. In some embodiments, the action automatically initiated by the application includes providing, for display on a user interface of the user device, one or more selectable ride hailing transportation options from a location corresponding to the user device and the ethanol sensor device. A user of the user device can select one or more of the selectable ride hailing transportation options on the user interface. In some embodiments, the user device action includes providing a plurality of selectable ride hailing transportation options from more than one application downloaded onto the user device. In some embodiments, one of the options includes an option for ride-sharing. In some embodiments, the application triggered by the user device action provides services corresponding to physical or mental health, wherein the application initiates the action by providing, for display on the user interface of the user device, one or more selectable physical or mental health services (e.g., options to purchase drinks including electrolytes at stores within walking distance, options to purchase a hot yoga class for the next day, options to purchase a meditation class the following day). In other embodiments, the application triggered by the user device action provides services corresponding to food orders or other types of goods (e.g., collectable items, designer goods), wherein the application initiates the action by providing, for display on the user interface of the user device, one or more selectable food orders or other orders for goods (e.g., options to purchase burgers or pizza to be delivered within a time period, options to purchase video games, options to purchase games provided by an application). In some embodiments, the user device action includes providing, via the application, one or more audio prompts, automatically providing one or more alerts or push-notifications, automatically providing an in-app notification, another type of user device action, or one or more combinations thereof.

At 204A, the ethanol sensor device 104 can receive an ethanol vapor concentration threshold from the server 116. For example, the ethanol vapor concentration threshold may be relative to a nitrogen concentration detected by the ethanol sensor device 104. In some embodiments, the ethanol sensor device 104 (e.g., also including a thermal conductivity sensor, an infrared gas sensor, or another type of nitrogen sensor) can transmit historical nitrogen concentration data and current nitrogen concentration data to the server 116 for determining the ethanol vapor concentration threshold. As another example, the ethanol vapor concentration threshold may be relative to an oxygen concentration detected by the ethanol sensor device 104. In some embodiments, the ethanol sensor device 104 (e.g., also including an electrochemical sensor or another type of oxygen sensor) can transmit historical oxygen concentration data and current oxygen concentration data to the server 116 for determining the ethanol vapor concentration threshold. In yet another example, the ethanol vapor concentration threshold may be relative to a carbon dioxide concentration detected by the ethanol sensor device 104. In some embodiments, the ethanol sensor device 104 (e.g., also including a non-dispersive infrared sensor or another type of carbon dioxide sensor) can transmit historical carbon dioxide concentration data and current carbon dioxide concentration data to the server 116 for determining the ethanol vapor concentration threshold.

At 204B, the ethanol sensor device 104 can transmit signals to the user device 102. For example a signal may include a short-range wireless communication signal, a 2.4 GHz signal, a 5 GHz signal, an RFID signal, an infrared signal, a low-power, short-range communication signal, a z-wave signal, another type of signal, or one or more combinations thereof. In some embodiments, the ethanol sensor device 104 can transmit signals for a particular duration and at particular time intervals. At 204C, the ethanol sensor device 104 can determine whether an ethanol vapor concentration is above a threshold. For example, the ethanol sensor device 104 can use one or more processors (e.g., one or more microprocessors, one or more CPUs, a digital signal processor, one or more cores, a host processor, a controller, a chip, a microchip, one or more circuits, a logic unit, an integrated circuit (IC), an application-specific IC (ASIC), any other suitable multi-purpose or specific processor or controller, or one or more combinations thereof).

At 204D, the ethanol sensor device 104 can communicate with the server 116. For example, in some embodiments, the server 116 determines that an ethanol vapor concentration is above a threshold. In some embodiments, the ethanol sensor device 104 can transmit an indication to the server 116 that the user device 102 is within a particular distance from the ethanol sensor device 104 (e.g., based on indoor positioning techniques performed by the ethanol sensor device 104) and that the ethanol vapor concentration is above the threshold. At 204E, the ethanol sensor device 104 can transmit a notification to the user device 102. For example, the notification may be provided via a messaging service or a data service and informs a user of the user device that it is unsafe for the user to operate a vehicle.

At 216A, the server 116 determines an ethanol vapor concentration threshold (e.g., based on historical vapor concentration data received from the ethanol sensor device 104). At 216B, the server 116 transmits the ethanol vapor concentration threshold to the ethanol sensor device 104 (e.g., via satellite 120 or cell site 112 of FIG. 1). At 216C, the server 116 receives communications from the user device 102 (e.g., a user device identifier) or the ethanol sensor device 104 (e.g., an indication that the ethanol vapor concentration is above the threshold). At 216D, the server 116 triggers an automatic user device action by the user device 102. For example, the user device action trigger may include causing the user device 102 to provide a push-notification via a particular application downloaded onto the user device (e.g., an application that provides services to alcoholics). In some embodiments, the push-notification (or another type of notification) may include one or more offers or discounts for a particular product or service (e.g., offers to attend meetings for alcoholics).

Figure 3:
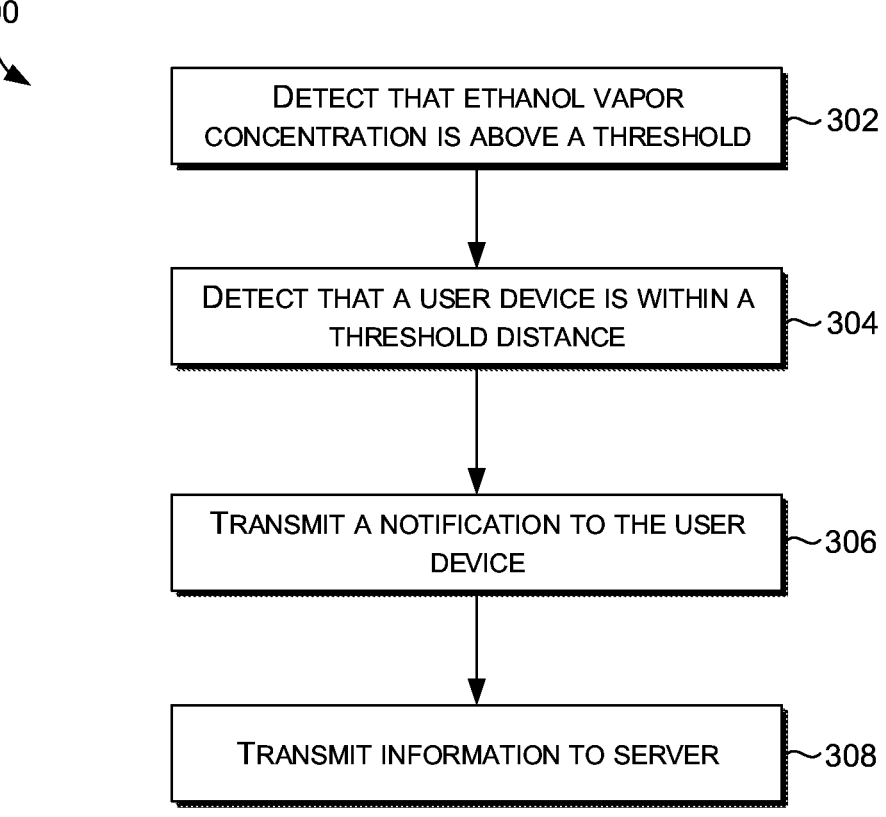
FIG. 3 depicts a flow diagram of an example ethanol sensor method corresponding to the ethanol sensors for location-based user device triggers, in accordance with aspects herein.

FIG. 3 depicts example flow diagram 300 for an ethanol sensor device. In embodiments, a plurality of ethanol sensor devices are each coupled to an object and are each configured to wirelessly detect ethanol vapors. In some embodiments, each of the plurality of ethanol sensor devices are positioned within a threshold distance from at least another one of the plurality of ethanol sensor devices. Each of the ethanol sensor device can also include one or more processors. At 302, a first ethanol sensor device of the plurality of ethanol sensor devices detects an ethanol vapor concentration that is above a threshold. In some embodiments, the ethanol vapor concentration is detected to be above the threshold relative to a nitrogen concentration detected by the first ethanol sensor device. In some embodiments, a second ethanol sensor device of the plurality of ethanol sensor devices detects a second ethanol vapor concentration that is above the threshold.

At 304, the first ethanol sensor device detects a user device that is within a threshold distance from the first ethanol sensor device. In some embodiments, the first ethanol sensor device detects that a plurality of user devices are within the threshold distance from the first ethanol sensor device and determines that the user device has a closest proximity to the first ethanol sensor device relative to each of the plurality of user devices. In some embodiments, the second ethanol sensor device detects a second user device that is within the threshold distance from the second ethanol sensor device. In some embodiments, the second ethanol sensor devices determines that the second user device has a closest proximity to the second ethanol sensor device relative to each of the plurality of user devices.

At 306, based on detecting that the ethanol vapor concentration is above the threshold and detecting that the user device is within the threshold distance, the first ethanol sensor device transmits a notification to the user device. In some embodiments, based on determining the user device has the closest proximity to the first ethanol sensor device, the first ethanol sensor device transmits the notification to the user device and transmits the information corresponding to the ethanol vapor concentration to the server. In some embodiments, the notification to the user device is provided via a messaging service informing a user of the user device that it is unsafe for the user to operate a vehicle. In some embodiments, the notification is transmitted to the second user device based on the second ethanol sensor device detecting that the second ethanol vapor concentration is above the threshold and based on the second ethanol sensor device detecting that the second user device is within the threshold distance.

At 308, based on detecting that the ethanol vapor concentration is above the threshold and detecting that the user device is within the threshold distance, the first ethanol sensor device transmits information to a server, such that the server can initiate an action via an application that is downloaded onto the user device. In some embodiments, the information transmitted to the server includes a user device identifier and a location of the user device. In some embodiments, based on detecting that the second ethanol vapor concentration is above the threshold and detecting that the second user device is within the threshold distance, the second ethanol sensor device transmits a set of information to the server such that the server can initiate the action via the application that is downloaded onto the second user device.

In some embodiments, the first ethanol sensor device transmits a request to a second ethanol sensor device of the plurality of ethanol sensor devices, the request for performing an indoor positioning technique for the user device. Further, the first ethanol sensor device receives, based on the request, indoor positioning information of the user device from the second ethanol sensor device. In addition, the first ethanol sensor device can transmit the information to the server, the information including an indoor position of the user device based at least in part on the indoor positioning information received from the second ethanol sensor device.

Figure 4:
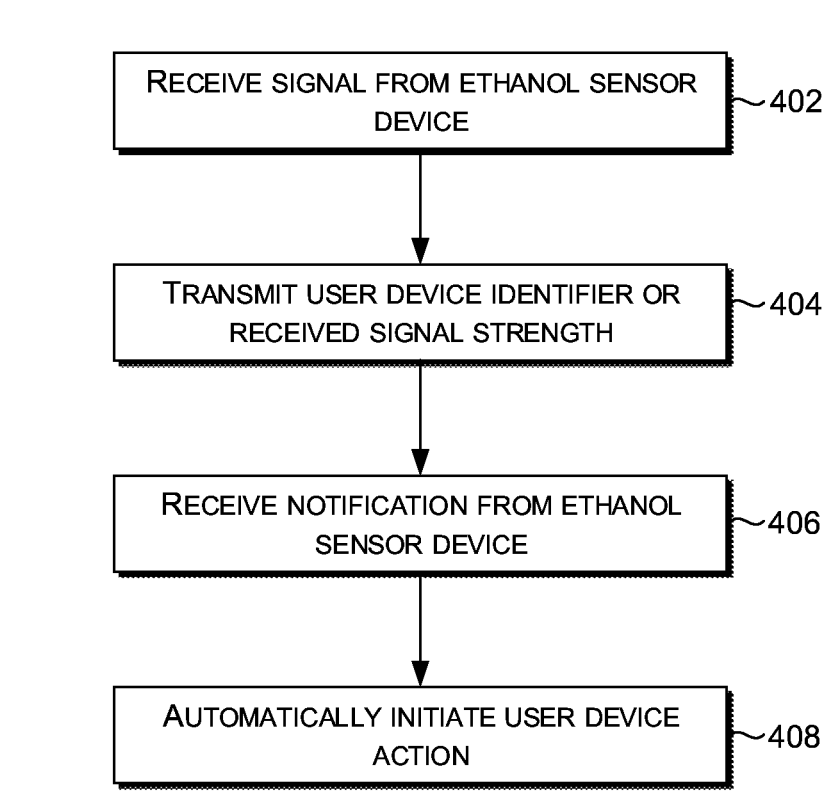
FIG. 4 depicts another flow diagram of an example user device method for the location-based user device triggers, in accordance with aspects herein.

FIG. 4 depicts example flow diagram 400 for a user device. At 402, the user device receives a signal from the ethanol sensor device. In some embodiments, the ethanol sensor device is a device remote from the user device and is affixed to an object located adjacent to an exit of an indoor environment. In some embodiments, the ethanol sensor device is a removable device that is attached to the user device via an input port. At 404, the user device transmits a user device identifier and a received signal strength to the ethanol sensor device or a server associated with the ethanol sensor device. At 406, the user device receives a notification from the ethanol sensor device, the notification received based on the ethanol sensor device detecting that an ethanol vapor concentration is above a threshold and based on the ethanol sensor device detecting that the user device is within a threshold distance from the ethanol sensor device. In some embodiments, the notification is received via a data service and includes information that it is unsafe for a user of the user device to operate a vehicle. At 408, based on transmitting the user device identifier and the received signal strength, the user device automatically initiates an action via an application that is downloaded onto the user device. In embodiments, the application provides ride hailing services, and wherein the action automatically initiated by the application includes providing, for display on a user interface of the user device, one or more selectable ride hailing transportation options from a location corresponding to the user device and the ethanol sensor device.

FIG. 5 depicts example flow diagram 500 for a server. At 502, the server is in communication with one or more ethanol sensor devices, and the server determines an ethanol vapor concentration threshold for the one or more ethanol sensor devices based on a location of each of the one or more ethanol sensor devices and historical user device traffic corresponding to the location of each of the one or more ethanol sensor devices. In some embodiments, the ethanol vapor concentration threshold is determined relative to historical oxygen concentrations and nitrogen concentrations (e.g., stored within database 114 of FIG. 1) detected by the ethanol sensor device. In some embodiments, the ethanol vapor concentration threshold is determined relative to historical carbon dioxide concentrations detected by the ethanol sensor device. For example, in some embodiments, the ethanol sensor devices can include, in addition to the ethanol sensors, a carbon dioxide sensor (e.g., a non-dispersive infrared sensor, an electrochemical sensor, a chemical gas sensor, a solid-state sensor), a nitrogen sensor (e.g., a thermal conductivity sensor, an infrared gas sensor), an oxygen sensor (e.g., an electrochemical sensor, an optical sensor, a paramagnetic sensor, a zirconia sensor, another type of oxygen sensor), another type of gas sensor, or one or more combinations thereof.

At 504, the server transmits a first ethanol vapor concentration threshold determined for a first ethanol sensor device of the one or more ethanol sensor devices to the first ethanol sensor device. In some embodiments, the server transmits a second ethanol vapor concentration threshold determined for a second ethanol sensor device of the one or more ethanol sensor devices to the second ethanol sensor device, the second ethanol vapor concentration threshold having a different value than the first ethanol vapor concentration. At 506, the server receives an indication from the first ethanol sensor device that a first ethanol vapor concentration is above the first ethanol vapor concentration threshold. In some embodiments, the server also receives a user device identifier for a user device. In some embodiments, the server can also receive (1) an indication from the second ethanol sensor device that a second ethanol vapor concentration is above the second ethanol vapor concentration threshold and (2) a second user device identifier for a second user device. For example, in some embodiments, the server receives the indication from the second ethanol sensor device and the second user device identifier simultaneously. In some embodiments, the server can compare the user device identifier and the second user device identifier to historical user device identifiers received from the one or more ethanol sensor devices over a period of time. In some embodiments, the server can also determine that the user device identifier or the second user device identifier has been identified by the one or more ethanol sensor devices over a threshold number of times over the period of time.

Based receiving the user device identifier and the indication that the first ethanol vapor concentration is above the first ethanol vapor concentration threshold, at 508, the server can transmit a trigger for an application that is downloaded onto the user device and that initiates an action by the application. In some embodiments, the server can also transmit the trigger for the application that is downloaded onto the second user device and that initiates the action by the application based receiving the second user device identifier and the indication that the second ethanol vapor concentration is above the second ethanol vapor concentration threshold, transmitting, by the one or more servers. In some embodiments, the application may provide ride hailing services, wherein the trigger initiates the action by the application including providing, for display on a user interface of the user device, one or more selectable ride hailing transportation options from a location corresponding to the user device. In some embodiments, the server also receives an indication of a selection by a user of the user device via the user interface to reserve a ride hailing transportation option, and the server can reserve the ride hailing transportation option for the user of the user device.

In some embodiments, the application provides services corresponding to physical or mental health, wherein the trigger initiates the action by the application including providing, for display on a user interface of the user device, one or more selectable physical or mental health services. Further, the server can compare the user device identifier to historical user device identifiers received from the one or more ethanol sensor devices over a period of time. In addition, the server can determine that the user device identifier has been identified by the one or more ethanol sensor devices over a threshold number of times over the period of time. The server can also provide for display on the user interface of the user device, the one or more selectable physical or mental health services based on the user device identifier being identified by the one or more ethanol sensor devices over the threshold number of times. In embodiments, the server can further receive an indication of a selection by a user of the user device via the user interface to reserve one of the one or more selectable physical or mental health services. The server can also reserve the one of the one or more selectable physical or mental health services for the user.

Example User Device

Having described the example embodiments discussed above of the presently disclosed technology, an example operating environment of an example user device (e.g., user device 102A of FIG. 1) is described below with respect to FIG. 6. User device 600 is but one example of a suitable computing environment and is not intended to suggest any particular limitation as to the scope of use or functionality of the technology disclosed. Neither should user device 600 be interpreted as having any dependency or requirement relating to any particular component illustrated, or a particular combination of the components illustrated in FIG. 6.

As illustrated in FIG. 6, example user device 600 includes a bus 602 that directly or indirectly couples the following devices: memory 604, one or more processors 606, one or more presentation components 608, one or more input/output (I/O) ports 610, one or more I/O components 612, a power supply 614, and one or more radios 616.

Bus 602 represents what may be one or more busses (such as an address bus, data bus, or combination thereof). Although the various blocks of FIG. 6 are shown with lines for the sake of clarity, in reality, these blocks represent logical, not necessarily actual, components. For example, one may consider a presentation component, such as a display device, to be an I/O component. Also, processors have memory. Accordingly, FIG. 6 is merely illustrative of an exemplary user device that can be used in connection with one or more embodiments of the technology disclosed herein.

User device 600 can include a variety of computer-readable media. Computer-readable media can be any available media that can be accessed by user device 600 and may include both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information, such as computer-readable instructions, data structures, program modules, or other data. Computer storage media includes, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage devices, or any other medium which can be used to store the desired information and which can be accessed by user device 600. Computer storage media does not comprise signals per se. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared, and other wireless media. One or more combinations of any of the above should also be included within the scope of computer-readable media.

Memory 604 includes computer storage media in the form of volatile and/or nonvolatile memory. The memory 604 may be removable, non-removable, or a combination thereof. Example hardware devices of memory 604 may include solid-state memory, hard drives, optical-disc drives, other hardware, or one or more combinations thereof. As indicated above, the computer storage media of the memory 604 may include RAM, Dynamic RAM, ROM, EEPROM, flash memory or other memory technology, CD-ROM, a cache memory, DVDs or other optical disk storage, magnetic cassettes, magnetic tape, magnetic disk storage or other magnetic storage devices, a short-term memory unit, a long-term memory unit, any other medium which can be used to store the desired information and which can be accessed by user device 600, or one or more combinations thereof.

The one or more processors 606 of user device 600 can read data from various entities, such as the memory 604 or the I/O component(s) 612. The one or more processors 606 may include, for example, one or more microprocessors, one or more CPUs, a digital signal processor, one or more cores, a host processor, a controller, a chip, a microchip, one or more circuits, a logic unit, an integrated circuit (IC), an application-specific IC (ASIC), any other suitable multi-purpose or specific processor or controller, or one or more combinations thereof. In addition, the one or more processors 606 can execute instructions, for example, of an operating system of the user device 600 or of one or more suitable applications.

The one or more presentation components 608 can present data indications via user device 600, another user device, or a combination thereof. Example presentation components 608 may include a display device, speaker, printing component, vibrating component, another type of presentation component, or one or more combinations thereof. In some embodiments, the one or more presentation components 608 may comprise one or more applications or services on a user device, across a plurality of user devices, or in the cloud. The one or more presentation components 608 can generate user interface features based on receiving the user device action trigger, the interface features including one or more of graphics, buttons, sliders, menus, lists, prompts, charts, audio prompts, alerts, vibrations, pop-ups, notification-bar or status-bar items, in-app notifications, other user interface features, or one or more combinations thereof.

The one or more I/O ports 610 allow user device 600 to be logically coupled to other devices, including the one or more I/O components 612, some of which may be built in. Example I/O components 612 can include a microphone, joystick, game pad, satellite dish, scanner, printer, wireless device, and the like. The one or more I/O components 612 may, for example, provide a natural user interface (NUI) that processes air gestures, voice, or other physiological inputs generated by a user. In some instances, the inputs the user generates may be transmitted to an appropriate network element for further processing. An NUI may implement any combination of speech recognition, touch and stylus recognition, facial recognition, biometric recognition, gesture recognition both on screen and adjacent to the screen, air gestures, head and eye tracking, and touch recognition associated with the one or more presentation components 608 on the user device 600. In some embodiments, the user device 600 may be equipped with one or more imaging devices, such as one or more depth cameras, one or more stereoscopic cameras, one or more infrared cameras, one or more RGB cameras, another type of imaging device, or one or more combinations thereof, (e.g., for gesture detection and recognition). Additionally, the user device 600 may, additionally or alternatively, be equipped with accelerometers or gyroscopes that enable detection of motion. In some embodiments, the output of the accelerometers or gyroscopes may be provided to the one or more presentation components 608 of the user device 600 to render immersive augmented reality or virtual reality.

The power supply 614 of user device 600 may be implemented as one or more batteries or another power source for providing power to components of the user device 600. In embodiments, the power supply 614 can include an external power supply, such as an AC adapter or a powered docking cradle that supplements or recharges the one or more batteries. In aspects, the external power supply can override one or more batteries or another type of power source located within the user device 600.

Some embodiments of user device 600 may include one or more radios 616 (or similar wireless communication components). The one or more radios 616 can transmit, receive, or both transmit and receive signals for wireless communications. In embodiments, the user device 600 may be a wireless terminal adapted to receive communications and media over various wireless networks. User device 600 may communicate using the one or more radios 616 via one or more wireless protocols, such as code division multiple access ("CDMA"), global system for mobiles ("GSM"), time division multiple access ("TDMA"), another type of wireless protocol, or one or more combinations thereof. In embodiments, the wireless communications may include one or more short-range connections (e.g., a Wi-Fi® connection, a Bluetooth connection, a near-field communication connection), a long-range connection (e.g., CDMA, GPRS, GSM, TDMA, 602.16 protocols), or one or more combinations thereof. In some embodiments, the one or more radios 616 may facilitate communication via radio frequency signals, frames, blocks, transmission streams, packets, messages, data items, data, another type of wireless communication, or one or more combinations thereof. The one or more radios 616 may be capable of transmitting, receiving, or both transmitting and receiving wireless communications via mmWaves, FD-MIMO, massive MIMO, 3G, 4G, 5G, 6G, another type of Generation, 802.11 protocols and techniques, another type of wireless communication, or one or more combinations thereof.

Having identified various components utilized herein, it should be understood that any number of components and arrangements may be employed to achieve the desired functionality within the scope of the present disclosure. For example, the components in the embodiments depicted in the figures are shown with lines for the sake of conceptual clarity. Other arrangements of these and other components may also be implemented. For example, although some components are depicted as single components, many of the elements described herein may be implemented as discrete or distributed components or in conjunction with other components, and in any suitable combination and location. Some elements may be omitted altogether. Moreover, various functions described herein as being performed by one or more entities may be carried out by hardware, firmware and/or software. For instance, various functions may be carried out by a processor executing instructions stored in memory. As such, other arrangements and elements (for example, machines, interfaces, functions, orders, and groupings of functions, and the like) can be used in addition to, or instead of, those shown.

Embodiments of the present disclosure have been described with the intent to be illustrative rather than restrictive. Embodiments described in the paragraphs above may be combined with one or more of the specifically described alternatives. In particular, an embodiment that is claimed may contain a reference, in the alternative, to more than one other embodiment. The embodiment that is claimed may specify a further limitation of the subject matter claimed. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims.

Many different arrangements of the various components depicted, as well as components not shown, are possible without departing from the scope of the claims below. Embodiments in this disclosure are described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims In the preceding detailed description, reference is made to the accompanying drawings which form a part hereof wherein like numerals designate like parts throughout, and in which is shown, by way of illustration, embodiments that may be practiced. It is to be understood that other embodiments may be utilized and structural or logical changes may be made without departing from the scope of the present disclosure. Therefore, the preceding detailed description is not to be taken in the limiting sense, and the scope of embodiments is defined by the appended claims and their equivalents.

The invention claimed is:

1. A system for utilizing ethanol sensor devices to initiate a user device trigger, the system comprising:

a plurality of ethanol sensor devices each coupled to an object and each configured to wirelessly detect ethanol vapors, wherein each of the plurality of ethanol sensor devices are positioned within a threshold distance from at least another one of the plurality of ethanol sensor devices; and one or more processors corresponding to each of the plurality of ethanol sensor devices, the one or more processors configured to perform operations comprising:

detecting, by a first ethanol sensor device of the plurality of ethanol sensor devices, an ethanol vapor concentration that is above a threshold;

detecting, by the first ethanol sensor device, a user device that is within a threshold distance from the first ethanol sensor device;

based on detecting that the ethanol vapor concentration is above the threshold and detecting that the user device is within the threshold distance, transmitting, by the first ethanol sensor device, a notification to the user device; and based on detecting that the ethanol vapor concentration is above the threshold and detecting that the user device is within the threshold distance, transmitting, by the first ethanol sensor device, information to a server, such that the server can initiate an action via an application that is downloaded onto the user device.

2. The system of claim 1, wherein the ethanol vapor concentration is detected to be above the threshold relative to a nitrogen concentration detected by the first ethanol sensor device.

3. The system of claim 1, the operations further comprising:

detecting, by the first ethanol sensor device, that a plurality of user devices are within the threshold distance from the first ethanol sensor device;

determining that the user device has a closest proximity to the first ethanol sensor device relative to each of the plurality of user devices; and based on determining the user device has the closest proximity, transmitting the notification to the user device and transmitting the information to the server.

4. The system of claim 1, wherein the notification to the user device is provided via a messaging service informing a user of the user device that it is unsafe for the user to operate a vehicle.

5. The system of claim 1, wherein the information transmitted to the server includes a user device identifier and a location of the user device.

6. The system of claim 1, the operations further comprising:

detecting, by a second ethanol sensor device of the plurality of ethanol sensor devices, a second ethanol vapor concentration that is above the threshold;

detecting, by the second ethanol sensor device, a second user device that is within the threshold distance from the second ethanol sensor device;

based on detecting that the second ethanol vapor concentration is above the threshold and detecting that the second user device is within the threshold distance, transmitting, by the second ethanol sensor device, the notification to the second user device; and based on detecting that the second ethanol vapor concentration is above the threshold and detecting that the second user device is within the threshold distance, transmitting, by the second ethanol sensor device, a set of information to the server such that the server can initiate the action via the application that is downloaded onto the second user device.

7. The system of claim 6, the operations further comprising:

detecting, by the second ethanol sensor device, that a plurality of user devices are within the threshold distance from the second ethanol sensor device, the plurality of user devices including the second user device;

determining that the second user device has a closest proximity to the second ethanol sensor device relative to each of the plurality of user devices; and based on determining the second user device has the closest proximity, transmitting the notification to the second user device and transmitting the set of information to the server.

8. The system of claim 1, the operations further comprising:

transmitting, by the first ethanol sensor device, a request to a second ethanol sensor device of the plurality of ethanol sensor devices, the request for performing an indoor positioning technique for the user device;

receiving, based on the request, indoor positioning information of the user device from the second ethanol sensor device; and transmitting the information to the server, the information including an indoor position of the user device based at least in part on the indoor positioning information received from the second ethanol sensor device.

9. A method for triggering an action by a user device based on communications with an ethanol sensor device, the method comprising:

receiving, by the user device, a signal from the ethanol sensor device;

transmitting, by the user device, a user device identifier and a received signal strength to the ethanol sensor device or a server associated with the ethanol sensor device;

receiving, by the user device, a notification from the ethanol sensor device, the notification received based on the ethanol sensor device detecting that an ethanol vapor concentration is above a threshold and based on the ethanol sensor device detecting that the user device is within a threshold distance from the ethanol sensor device; and based on transmitting the user device identifier and the received signal strength, automatically initiating, by the user device, an action via an application that is downloaded onto the user device.

10. The method of claim 9, wherein the application provides ride hailing services, and wherein the action automatically initiated by the application includes providing, for display on a user interface of the user device, one or more selectable ride hailing transportation options from a location corresponding to the user device and the ethanol sensor device.

11. The method of claim 9, wherein the notification is received via a data service and includes information that it is unsafe for a user of the user device to operate a vehicle.

12. The method of claim 9, wherein the ethanol sensor device is a device remote from the user device and is affixed to an object located adjacent to an exit of an indoor environment.

13. The method of claim 9, wherein the ethanol sensor device is a removable device that is attached to the user device via an input port.

14. One or more non-transitory computer storage media having computer-executable instructions embodied thereon, that when executed by at least one processor, cause the at least one processor to perform a method for initiating a user device trigger based on communications with an ethanol sensor device, the method comprising:

determining, by one or more servers in communication with one or more ethanol sensor devices, an ethanol vapor concentration threshold for the one or more ethanol sensor devices based on a location of each of the one or more ethanol sensor devices and historical user device traffic corresponding to the location of each of the one or more ethanol sensor devices;

transmitting, by the one or more servers, a first ethanol vapor concentration threshold determined for a first ethanol sensor device of the one or more ethanol sensor devices to the first ethanol sensor device;

receiving, by the one or more servers, an indication from the first ethanol sensor device that a first ethanol vapor concentration is above the first ethanol vapor concentration threshold;

receiving, by the one or more servers, a user device identifier for a user device; and based receiving the user device identifier and the indication that the first ethanol vapor concentration is above the first ethanol vapor concentration threshold, transmitting, by the one or more servers, a trigger for an application that is downloaded onto the user device and that initiates an action by the application.

15. The non-transitory computer-readable media of claim 14, wherein the method further comprises:

transmitting, by the one or more servers, a second ethanol vapor concentration threshold determined for a second ethanol sensor device of the one or more ethanol sensor devices to the second ethanol sensor device, the second ethanol vapor concentration threshold having a different value than the first ethanol vapor concentration;

receiving, by the one or more servers, an indication from the second ethanol sensor device that a second ethanol vapor concentration is above the second ethanol vapor concentration threshold;

receiving, by the one or more servers, a second user device identifier for a second user device; and based receiving the second user device identifier and the indication that the second ethanol vapor concentration is above the second ethanol vapor concentration threshold, transmitting, by the one or more servers, the trigger for the application that is downloaded onto the second user device and that initiates the action by the application.

16. The non-transitory computer-readable media of claim 14, wherein the first ethanol vapor concentration threshold is determined relative to historical oxygen concentrations and nitrogen concentrations detected by the ethanol sensor device.

17. The non-transitory computer-readable media of claim 14, wherein the application provides ride hailing services, wherein the trigger initiates the action by the application including providing, for display on a user interface of the user device, one or more selectable ride hailing transportation options from a location corresponding to the user device, and wherein the method further comprises:

receiving an indication of a selection by a user of the user device via the user interface to reserve a ride hailing transportation option; and reserving the ride hailing transportation option for the user of the user device.

18. The non-transitory computer-readable media of claim 14, wherein the application provides services corresponding to physical or mental health, wherein the trigger initiates the action by the application including providing, for display on a user interface of the user device, one or more selectable physical or mental health services, and wherein the method further comprises:

comparing the user device identifier to historical user device identifiers received from the one or more ethanol sensor devices over a period of time;

determining that the user device identifier has been identified by the one or more ethanol sensor devices over a threshold number of times over the period of time; and providing, for display on the user interface of the user device, the one or more selectable physical or mental health services based on the user device identifier being identified by the one or more ethanol sensor devices over the threshold number of times.

19. The non-transitory computer-readable media of claim 18, the method further comprising:

receiving an indication of a selection by a user of the user device via the user interface to reserve one of the one or more selectable physical or mental health services; and reserving the one of the one or more selectable physical or mental health services for the user.

20. The non-transitory computer-readable media of claim 14, wherein the first ethanol vapor concentration threshold is determined relative to historical carbon dioxide concentrations detected by the ethanol sensor device.

* * * * *